United States Patent [19]

Berg et al.

[11] Patent Number: 4,642,166

[45] Date of Patent: Feb. 10, 1987

[54] DEHYDRATION OF FORMIC ACID BY EXTRACTIVE DISTILLATION

[76] Inventors: Lloyd Berg; An-I Yeh, both of 1314 S. Third Ave., Bozeman, Mont. 59715

[21] Appl. No.: 827,891

[22] Filed: Feb. 10, 1986

[51] Int. Cl.[4] .......................... B01D 3/40; C07C 53/02
[52] U.S. Cl. ........................................ 203/15; 203/51; 203/56; 203/57; 203/58; 203/60; 203/61; 203/62; 203/64; 562/609
[58] Field of Search ................... 203/15, 16, 57, 51, 203/58, 64, 60–62, 56; 562/609, 606, 608

[56] References Cited

U.S. PATENT DOCUMENTS

| | | | |
|---|---|---|---|
| 2,038,865 | 4/1936 | Wentworth et al. | 203/58 |
| 2,368,597 | 1/1945 | Morris et al. | 203/58 |
| 4,024,028 | 5/1977 | Haskell | 203/57 |
| 4,076,594 | 2/1978 | Buelow et al. | 203/58 |
| 4,576,683 | 3/1986 | Cohen | 203/15 |

*Primary Examiner*—Wilbur Bascomb

[57] ABSTRACT

Formic acid cannot be completely removed from formic acid - water mixtures by distillation because of the presence of the maximum azeotrope. Formic acid can be readily removed from mixtures containing it and water by using extractive distillation in which the extractive distillation agent is a sulfone. Typical examples of effective agents are thiophan sulfone; dimethyl sulfone and adiponitrile; phenyl sulfone, adiponitrile and acetophenone.

11 Claims, No Drawings

DEHYDRATION OF FORMIC ACID BY EXTRACTIVE DISTILLATION

FIELD OF THE INVENTION

This invention relates to a method for dehydrating formic acid using certain higher boiling liquids as the agent in extractive distillation.

DESCRIPTION OF PRIOR ART

Extractive distillation is the method of separating close boiling compounds or azeotrodes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixtures and the extracted agent are continuously removed from the column. The usual methods of separation of these two components are the use of another rectification column, cooling and phase separation or solvent extraction.

There are currently two commercial methods for manufacturing formic acid. One is the reaction of caustic soda with carbon monoxide under pressure to produce sodium formate. This is then hydrolysed with sulfuric acid to yield the formic acid. The other is to obtain the formic acid as a by-product from the oxidation of n-butane. Both of these processes yield an aqueous mixture of formic acid. However the components of this mixture cannot be separated by conventional rectification because formic acid boils at 100.8° C., only 0.8° C. above water and because these two form a maximum azeotrope boiling at 107.2° C. and containing 22.5 wt. % water. Thus it is impossible to separate completely formic acid from water by rectification because of the closeness of the boiling points and because as soon as the maximum azeotrope composition is attained, no further change in composition will occur.

Extractive distillation would be an attractive method of effecting the separation of formic acid from water if agents can be found that (1) will break the formic acid-water azeotrope and (2) are easy to recover from formic acid, that is, form no azeotrope with formic acid and boil sufficiently above formic acid to make the separation by rectification possible with only a few theoretical plates.

Extractive distillation typically requires the addition of an equal amount to twice as much extractive agent as the formic acid-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

The breaking of this azeotrope by extractive distillation is a new concept. Recent attempts to separate formic acid from water were reported by Kokai, Japanese Patent No. 82 24,324, Feb. 8, 1982 who used amines or phosohate esters to separate formic acid from water. Kawabata, Higuchi & Yoshida, J. Bull. Chem. Soc. Japan, 1981, 54(11), 3253-8 used poly(4-vinylpyridine) to remove the water from formic acid. Jahn, East German Patent No. 133,559, Jan. 10, 1979 separated acetic acid-formic acid-water mixtures in three successive columns and only got a partial dehydration of the formic acid.

OBJECTIVE OF THE INVENTION

The object of this invention is to provide a process or method of extractive distillation that will enhance the relative volatility of water from formic acid in their separation in a rectification column. It is a further object of this invention to identify suitable extractive distillation agents which will eliminate the formic acid-water azeotrope and make possible the production of pure formic acid and water by rectification. It is a further object of this invention to identify organic compounds which in addition to the above constraints, are stable, can be separated from formic acid by rectification with relatively few theoretical plates and can be recycled to the extractive distillation column and reused with little decomposition.

SUMMARY OF THE INVENTION

The objects of the invention are provided by a process for separating formic acid from water which entails the use of sulfolanes, either alone or admixed with certain oxygenated organic compounds.

DETAILED DESCRIPTION OF THE INVENTION

We have discovered that sulfolanes, either alone or admixed with other organic compounds, will effectively negate the formic acid-water maximum azeotrope and permit the separation of pure water from formic acid by rectification when employed as the agent in extractive distillation. Table 1 lists several sulfolanes and their mixtures and the approximate proportions that we have found to be effective. The data in Table 1 was obtained is a vapor-liquid equilibrium still. In each case, the starting material was the formic acid-water azeotrope. The ratios are the parts by weight of extractive agent used per part of formic acid-water azeotrope. The relative volatilities are listed for each of the two ratios ceed as if the azeotrope no longer existed and brings the more volatile component, water, out as overhead. And this from formic acid which normally boils only 0.8° C. higher. It is our belief that this is the first time that this has been accomplished for this azeotrope.

TABLE 1

Extractive Distillation Agents Containing Sulfones

| Compounds | Ratios | | Relative Volatilities | |
|---|---|---|---|---|
| Sulfolane | 1 | 6/5 | 2.11 | 2.04 |
| Sulfolane, Adiponitrile | $(\frac{1}{2})^2$ | $(3/5)^2$ | 3.28 | 3.93 |
| Sulfolane, Methylglutaronitrile | " | " | 2.79 | 3.28 |
| Sulfolane, Phenyl acetic acid | " | " | 1.80 | 1.97 |
| Sulfolane, Salicylic acid | " | " | 3.63 | 4.94 |
| Sulfolane, Salicylic acid, Acetophenone | $(\frac{1}{3})^3$ | $(2/5)^3$ | 2.58 | 3.14 |
| Sulfolane, Salicylic acid, Adiponitrile | " | " | 2.88 | 4.08 |
| Sulfolane, Methyl glutaronitrile, Adiponitrile | " | " | 2.59 | 2.94 |
| Sulfolane, Methyl glutaronitrile, Benzophenone | " | " | 2.67 | 3.27 |
| Dimethyl sulfone, Adiponitrile | $(\frac{1}{2})^2$ | $(3/5)^2$ | 2.65 | 3.64 |
| Dimethyl sulfone, Adiponitrile, Acetophenone | $(\frac{1}{3})^3$ | $(2/5)^3$ | 3.37 | 2.90 |
| Phenyl sulfone, Adiponitrile | $(\frac{1}{2})^2$ | $(3/5)^2$ | 2.08 | 1.62 |
| Phenyl sulfone, Adiponitrile, Acetophenone | $(\frac{1}{3})^3$ | $(2/5)^3$ | 2.73 | 4.58 |
| Dihydroxydiphenylsulfone, Adiponitrile | $(\frac{1}{2})^2$ | $(3/5)^2$ | 1.92 | 3.32 |
| Dihydroxydiphenylsulfone, Adiponitrile, Acetophenone | $(\frac{1}{3})^3$ | $(2/5)^3$ | 3.32 | 3.22 |
| Butadiene sulfone, Adiponitrile | $(\frac{1}{2})^2$ | | 2.21 | — |
| Sulfolane, Ethylene glycol | " | $(3/5)^2$ | 3.20 | 3.12 |
| Sulfolane, Ethylene glycol, 2,4-Pentanedione | $(\frac{1}{3})^3$ | $(2/5)^3$ | 3.06 | 3.30 | employed. The compound which is effective when used alone is sulfolane. The compounds which are effective when used in mixtures are dimethyl sulfone, phenyl sulfone, dihydroxydiphenyl sulfone, butadiene sulfone, adiponitrile, methyl glutaronitrile, phenyl acetic acid, salicylic acid, acetophenone and benzophenone. The two relative volatilities shown in Table 1 correspond to the two different ratios investigated. For example, in Table 1, one part of sulfolane with one part of the formic acid-water azeotrope gives a relative volatility of 2.11, 6/5 parts of sulfolane give 2.04. One half part of sulfolane mixed with one half part of adiponitrile with one part of the formic acid-water azeotrope gives a relative volatility of 3.28, 3/5 parts of sulfolane plus 3/5 parts of adiponitrile give 3.93. One third part of dimethyl sulfone plus ⅓ part of adiponitrile plus ⅓ part of acetophenone with one part of the formic acid-water azeotrope gives a relative volatility of 3.37, with 2/5 parts, these three give a relative volatility of 2.90. In every example in Table 1, the starting material is the formic acid-water azeotrope which possesses a relative volatility of 1.00.

One of the compounds, sulfolane, listed in Table 1 and whose relative volatility had been determined in the vapor-liquid equilibrium still, was then evaluated in a glass perforated plate rectification column possessing 4.5 theoretical plates and the results listed in Table 2. The data in Table 2 was obtained in the following manner. The charge was 85 wt. % formic acid and 15% water and after a half hour of operation in the 4.5 theoretical plate column to establish equilibrium, sulfolane at 95° C. and 20 ml/min. was pumped in. The rectification was continued with sampling of overhead and bottoms after one hour. The analysis is shown in Table 2 and was 99.5% water, 0.5% formic acid in the overhead and 26.1% water, 73.9% formic acid in the bottoms which gives a relative volatility of 4.09 of water to formic acid. This indicates that the maximum azeotrope has been negated and separation accomplished. Without the extractive agent, the overhead would have approached the maximum azeotrope composition of 22.5% water. This proves that the extractive agent is negating the azeotrope and makes the rectification pro-

TABLE 2

Data From Run Made In Rectification Column With Sulfolane

| | Wt. % - 1 hr. | Wt. % - 1.5 hrs. |
|---|---|---|
| Overhead - Water | 99.5 | 99.4 |
| Formic Acid | 0.5 | 0.6 |
| Bottoms - Water | 26.1 | 30.5 |
| Formic Acid | 73.9 | 69.5 |
| Relative Volatility | 4.09 | 4.02 |

THE USEFULNESS OF THE INVENTION

The usefulness or utility of this invention can be demonstrated by referring to the data presented in Tables 1 and 2. All of the successful extractive distillation agents show that formic acid and water can be separated from their maximum azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity formic acid from any mixture with water including the maximum azeotrope. The stability of the compounds used and the boiling point difference is such that complete recovery and recycle is obtainable by a simple distillation and the amount required for make-up is small.

WORKING EXAMPLES

EXAMPLE 1

Fifty grams of the formic acid-water azeotrope and fifty grams of sulfolane were charged to an Othmer type glass vapor-liquid equilibrium still and refluxed for five hours. Analysis of the vapor and liquid by gas chromatography gave vapor 36% water, 64% formic acid; liquid of 21% water, 79% formic acid. This indicates a relative volatility of 2.11. Ten grams of sulfolane were added and refluxing continued for another fourteen hours. Analysis indicated a vapor composition of 37.5% water, 62.5% formic acid; a liquid composition of 18.5% water, 81.5% formic acid which is a relative volatility of 2.04.

EXAMPLE 2

Fifty grams of the formic acid-water azeotrope, 25 grams of sulfolane and 25 grams of adiponitrile were charged to the vapor-liquid equilibrium still and refluxed for ten hours. Analysis indicated a vapor composition of 34% water, 66% formic acid, a liquid composition of 12% water, 88% formic acid which is a relative volatility of 3.28. Five grams of sulfolane and five grams of adiponitrile were added and refluxing continued for another twelve hours. Analysis indicated a vapor composition of 40% water, 60% formic acid, liquid composition of 14.5% water, 85.5% formic acid which is a relative volatility of 3.93.

EXAMPLE 3

Fifty grams of the formic acid-water azeotrope, 17 grams of dimethylsulfone, 17 grams of adiponitrile and 17 grams of acetophenone were charged to the vapor-liquid equilibrium still and refluxed for eleven hours. Analysis indicated a vapor composition of 40% water, 60% formic acid a liquid composition of 16.5% water, 83.5% formic acid which is a relative volatility of 3.37. Three grams each of dimethylsulfone, adiponitrile and acetophenone were added and refluxing continued for another 12 hours. Analysis indicated a vapor composition of 42% water, 58% formic acid, a liquid composition of 20% water, 80% formic acid which is a relative volatility of 2.90.

EXAMPLE 4

A glass perforated plate rectification column was calibrated with ethylbenzene and p-xylene which possesses a relative volatility of 1.06 and found to have 4.5 theoretical plates. A solution comprising 340 grams of formic acid and 60 grams of water was placed in the stillpot and heated. When refluxing began, an extractive agent consisting of pure sulfolane was pumped into the column at a rate of 20 ml/min. The temperature of the extractive agent as it entered the column was 95° C. After establishing the feed rate of the extractive agent, the heat input to the formic acid and water in the stillpot was adjusted to give a total reflux rate of 10–20 ml/min. After one hour of operation, the overhead and bottoms samples of approximately two ml. were collected and analysed using gas chromatography. The overhead analysis was 99.5% water, 0.5% formic acid. The bottoms analysis was 26.1% water, 73.9% formic acid. Using these compositions in the Fenske equation, with the number of theoretical plates in the column being 4.5, gave an average relative volatility of 4.09 for each theoretical plate. After 1½ hours of total operating time, the overhead and bottoms samples were again taken and analysed. The overhead composition was 99.4% water, 0.6% formic acid and the bottoms composition was 30.5% water, 69.5% formic acid. This gave an average relative volatility of 4.02 for each theoretical plate.

The nature of the present invention having been described, what we wish to claim as new and useful and secure by Letters Patent is:

1. A method for recovering formic acid from a mixture of formic acid and water which comprises distilling a mixture of formic acid and water in a rectification column in the presence of about one part of extractive agent per part of formic acid-water mixture, recovering water as overhead product and obtaining the formic acid and extractive agent from the stillpot, the extractive agent comprises at least a sulfone.

2. The method of claim 1 in which the extractive agent comprises thiophan sulfone (sulfolane).

3. The method of claim 1 in which the extractive agent comprises dimethyl sulfone.

4. The method of claim 1 in which the extractive agent comprises phenyl sulfone.

5. The method of claim 1 in which the extractive agent comprises dihydroxydiphenyl sulfone.

6. The method of claim 1 in which the extractive agent comprises butadiene sulfone.

7. The method of claim 1 in which the extractive agent comprises a mixture of thiophan sulfone (sulfolane) and at least one material from the group consisting essentially of adiponitrile, methyl glutaronitrile, phenyl acetic acid, salicylic acid, acetoohenone, benzophenone, ethylene glycol and 2,4-pentanedione.

8. The method of claim 1 in which the extractive agent comprises a mixture of dimethyl sulfone and at least one material from the group consisting essentially of adiponitrile and acetophenone.

9. The method of claim 1 in which the extractive agent comprises a mixture of phenyl sulfone and at least one material from the group consisting essentially of adiponitrile and acetophenone.

10. The method of claim 1 in which the extractive agent comprises a mixture of dihydroxdiphenyl sulfone and at least one material from the group consisting essentially of adiponitrile and acetophenone.

11. The method of claim 1 in which the extractive agent comprises a mixture of butadiene sulfone and adiponitrile.

* * * * *